United States Patent
Pye

(10) Patent No.: US 6,914,144 B2
(45) Date of Patent: Jul. 5, 2005

(54) PROCESS FOR PREPARING INTEGRIN ANTAGONIST INTERMEDIATE

(75) Inventor: Philip J. Pye, Guttenberg, NJ (US)

(73) Assignee: Merck & Co., Inc., Rahway, NJ (US)

( * ) Notice: Subject to any disclaimer, the term of this patent is extended or adjusted under 35 U.S.C. 154(b) by 9 days.

(21) Appl. No.: 10/353,612

(22) Filed: Jan. 29, 2003

(65) Prior Publication Data

US 2003/0176707 A1 Sep. 18, 2003

Related U.S. Application Data

(60) Provisional application No. 60/352,601, filed on Jan. 29, 2002.

(51) Int. Cl.[7] .................. C07D 213/38; C07D 213/53
(52) U.S. Cl. .............................. 546/329; 546/350
(58) Field of Search ................................ 546/350, 329

(56) References Cited

U.S. PATENT DOCUMENTS

| | | |
|---|---|---|
| 6,017,926 A | 1/2000 | Askew et al. |
| 6,262,268 B1 | 7/2001 | Palucki et al. |
| 6,262,286 B1 | 7/2001 | Gregorius et al. |

OTHER PUBLICATIONS

Palucki, et al., Tetrahedron Letters, vol. 42, No. 39, 2001) "A highly efficient synthesis of 2–[3–aminopropyl]–5m6,7, 8–tetrahydronaphthyridine via a double Suzuki reaction and a Chichibabin cyclization", pp. 6811–6814.

*Primary Examiner*—Cecilia Tsang
*Assistant Examiner*—Raymond Covington
(74) *Attorney, Agent, or Firm*—Patricia A. Shatynski; Mark R. Daniel

(57) ABSTRACT

A process is provided for the preparation of 2,5-di-(3'-aminopropyl)pyridine which is useful in the synthesis of αvβ3 integrin receptor antagonists. Also provided are useful intermediates obtained from the process.

13 Claims, No Drawings

PROCESS FOR PREPARING INTEGRIN ANTAGONIST INTERMEDIATE

This application claims the priority of Provisional Application No. 60/352,601, filed Jan. 29, 2002.

FIELD OF THE INVENTION

The present invention discloses a novel process and novel intermediates toward the preparation of 2,5-di-(3'-aminopropyl)pyridine which is useful in the synthesis of αvβ3 integrin receptor antagonists.

BACKGROUND OF THE INVENTION

The present invention provides a novel process for the preparation of 2,5-di-(3'-aminopropyl)pyridine of structural formula I.

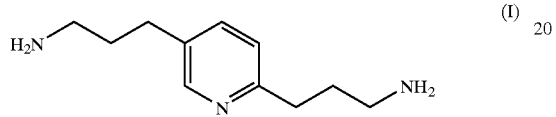

Another aspect of the present invention is concerned with novel intermediates useful in the disclosed process.

A synthesis of the compound of formula I was previously disclosed in U.S. Pat. No. 6,262,268 (Jul. 17, 2001). In the issued U.S. patent, the 2,5-bis-substituted pyridine ring system was constructed by means of a one-pot double Suzuki cross-coupling of a 2,5-dihalopyridine with a protected allylamine in the presence of 9-BBN and subsequent removal of the primary amine protecting groups.

In the present invention, the compound of formula I is produced in a highly efficient manner in a total of four chemical steps featuring a one-pot double addition of acetonitrile anion to a 2,5-pyridine dicarboxylate diester followed by activation of the resulting di-enolate and a two-step hydrogenation sequence to the final product.

SUMMARY OF THE INVENTION

The instant invention is concerned with an alternative process for preparing 2,5-di-(3'-aminopropyl)pyiidine of structural formula I and useful intermediates obtained during that process. The process utilizes a double addition of acetonitrile anion to a 2,5-pyridine dicarboxylate diester, activation of the resulting di-enolate, and a two-step hydrogenation sequence to the diamine I.

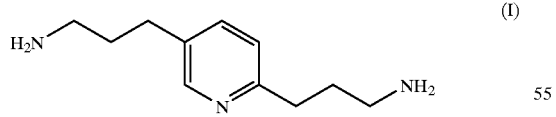

The novel process and novel intermediates are illustrated in the following embodiment denoted in Scheme 1 below.

Scheme 1

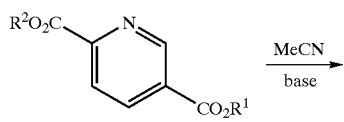

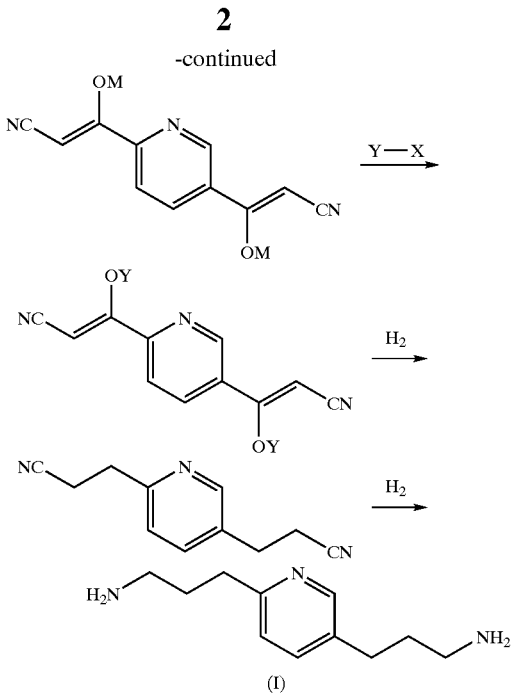

DETAILED DESCRIPTION OF THE INVENTION

The process of the present invention involves the preparation of the compound of structural formula I:

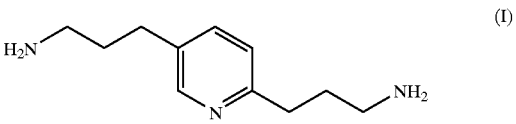

comprising the steps of: (a) producing a compound of structural formula II:

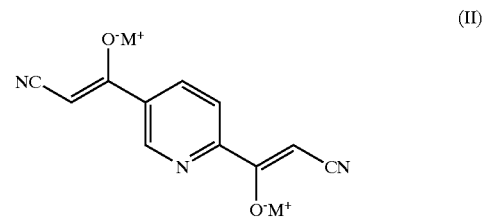

wherein M is an alkali or alkaline earth metal, by treating a 2,5-pyridine dicarboxylate diester of structural formula III:

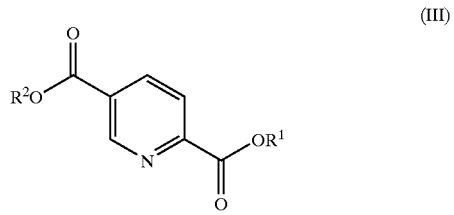

wherein $R^1$ and $R^2$ are each independently $C_{1-4}$ alkyl or phenyl-$C_{1-3}$ alkyl, with acetonitrile in a reaction solvent in the presence of a base; (b) producing a compound of structural formula IV:

(IV)

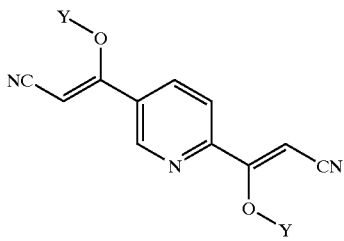

wherein Y is an acyl, sulfonyl, or phosphoryl group, by reacting a compound of structural formula II:

(II)

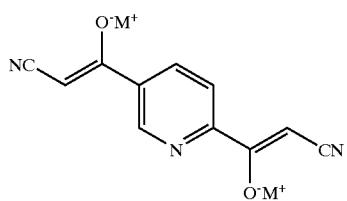

with an acylating, sulfonylating, or phosphorylating reagent; (c) producing a compound of structural formula VI:

(VI)

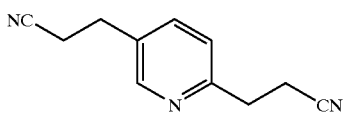

by hydrogenating a compound of structural formula IV:

(IV)

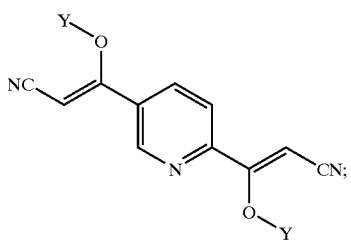

and (d) producing a compound of structural formula I:

(I)

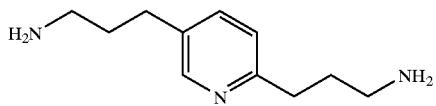

by hydrogenating a compound of structural formula VI:

(VI)

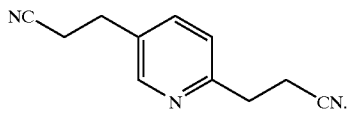

Compound I may be isolated from the reaction or used without further purification for additional chemical modification in the synthesis of αvβ3 integrin receptor antagonists.

The key steps in the process of the present invention include a double acetonitrile addition to a 2,5-pyridine dicarboxylate diester, activation of the resulting di-enolate, and a two-step hydrogenation sequence to the final product.

The substrate for the double acetonitrile addition reaction is a 2,5-pyridine dicarboxylate diester of structural formula III wherein $R^1$ and $R^2$ are each independently $C_{1-4}$ alkyl or phenyl-$C_{1-3}$ alkyl. In one embodiment, the dicarboxylate diester is a dimethyl or diethyl ester ($R^1=R^2=Me$ or Et, respectively).

The double acetonitrile addition reaction is effected with a 2,5-pyridine dicarboxylate diester and acetonitrile in the presence of a base in a suitable reaction solvent. In one embodiment, the base is selected from the group consisting of an alkali or alkaline earth metal hydride, such as sodium hydride, lithium hydride, magnesium hydride, and calcium hydride; an alkyl lithium, such as n-butyl lithium; an alkali metal hexamethyidisilazide, such as potassium and lithium hexamethyldisilazide; and an alkali or alkaline earth metal alkoxide, such as sodium methoxide, sodium ethoxide, and potassium tert-butoxide. In one class of this embodiment, the base is an alkali or alkaline earth hydride, in particular, sodium hydride or calcium hydride. Suitable reaction solvents for the addition reaction include, but are not limited to, toluene, benzene, acetonitrile, dioxane, diethyl ether, tetrahydrofuran, and dialkyl ethylene glycol ethers, such as ethylene glycol dimethyl ether. In one embodiment the reaction solvent is acetonitrile or ethylene glycol dimethyl ether. The addition reaction is carried out at a temperature range of about 0° C. to about 10° C. In one embodiment, the addition reaction is carried out at a temperature range of about 70° C. to about 80° C.

The second step in the process of the present invention involves the activation of the dienolate of structural formula II. This is effected by treating the dienolate II in a suitable reaction solvent with an acylating, sulfonylating, or phosphorylating reagent Y-X, wherein Y is an acyl, sulfonyl, or phosphoryl group, respectively, and X is a leaving group, such as halide, acyloxy, and sulfonyloxy. Examples of an acylating reagent include an alkanoyl halide, an alkanecarboxylic acid anhydride, an aroyl halide, wherein aroyl is benzoyl or naphthoyl, and an arylcarboxylic acid anhydride, wherein aryl is phenyl or naphthyl. Examples of a sulfonylating agent include an alkanesulfonyl halide, an alkanesulfonic anhydride, an arylsulfonyl halide, and an arylsulfonic anhydride, wherein aryl is phenyl or naphthyl. Examples of a phosphorylating agent include a dialkylphosphoryl halide and a diarylphosphoryl halide. Specific embodiments of the reagent Y-X include methanesulfonyl chloride, methanesulfonic anhydride, trifluoromethanesulfonyl chloride, trifluoromethanesulfonic anhydride, benzenesulfonyl chloride, p-toluenesulfonyl chloride, p-toluenesulfonic anhydride, acetyl chloride, acetic anhydride, pivaloyl chloride, pivalic anhydride, benzoyl chloride, and benzoic anhydride. In a preferred embodiment the reagent Y-X is benzenesulfonyl chloride or p-toluenesulfonyl chloride. Suitable reaction solvents include, but are not limited to, lower alkanols, such as methanol, ethanol, and isopropyl alcohol; toluene; tetrahydrofuran; methylene chloride; water; ethyl acetate; isopropyl acetate; and aqueous lower alkanols. In one embodiment the reaction solvent is methanol or ethanol. The reaction is carried out at a temperature range of about −10° C. to about 30° C. A buffer is optionally added to the reaction mixture. In one embodiment the buffer is sodium carbonate, potassium carbonate, or dipotassium hydrogenphosphate.

The third reaction step involves hydrogenation of the activated enolate of structural formula IV. In one embodiment, the hydrogenation reaction is performed by applying hydrogen in the presence of a palladium catalyst and base in a suitable reaction solvent. Palladium catalysts include Pd/C, Pd/Al$_2$O$_3$, Pd/CaCO$_3$, Pd/BaCO$_3$, Pd/BaSO$_4$, and Pd(OH)$_2$. The base is selected from an inorganic base or an organic base. Inorganic bases include sodium carbonate, potassium carbonate, dipotassium hydrogenphosphate, and potassium dihydrogenphosphate. Organic bases include pyridine and substituted pyridines, such as 2,6-lutidine, 2,4,6-collidine, and polyvinylpyridine. Suitable reaction solvents include, but are not limited to, toluene; tetrahydrofuran; lower alkanols, such as methanol and ethanol; water; and aqueous lower alkanols, such as aqueous methanol and aqueous ethanol.

The fourth reaction in the sequence involves hydrogenation of the derived di(cyanoethyl)2,5-pyridine of structural formula VI. In one embodiment, this reaction is performed in a suitable reaction solvent in the presence of a Raney nickel catalyst and ammonia. Suitable reaction solvents include, but are not limited to, toluene; tetrahydrofuran; lower alkanols, such as methanol and ethanol; water; and aqueous lower alkanols, such as aqueous methanol and aqueous ethanol.

Another aspect of the present invention provides novel compounds of structural formula IV which are intermediates in the instant process for the preparation of compound I:

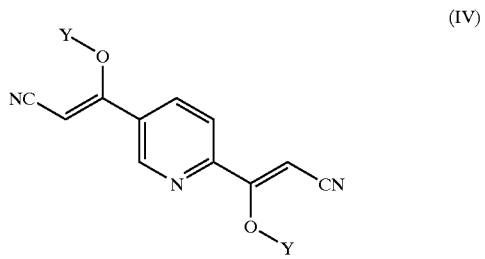

(IV)

wherein Y is C$_{1-4}$ alkanoyl, benzoyl, naphthoyl, phenyl-C$_{1-3}$ alkanoyl, C$_{1-4}$ alkanesulfonyl, benzenesulfonyl, di-(C$_{1-4}$ alkyl)phosphoryl, and diphenylphosphoryl, wherein the benzene, benzoyl, naphthoyl, and phenyl groups are unsubstituted or substituted with one or two substituents independently selected from halogen, nitro, cyano, methyl, and methoxy. In one embodiment, Y is benzenesulfonyl optionally substituted with one or two substituents independently selected from halogen, nitro, cyano, methyl, and methoxy.

A further aspect of the present invention provides the novel compound of structural formula VI which is an intermediate in the instant process for the preparation of compound I:

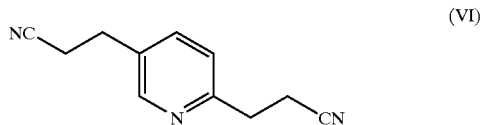

(VI)

The compound of structural formula I can be converted into 3-(5,6,7,8-tetrahydro-[1,8]-naphthyridin-2-yl)-propylamine (VII) as described in U.S. Pat. No. 6,262,268 (Jul. 17, 2001). As disclosed in WO 01134602, this intermediate is useful to prepare αvβ3 integrin receptor antagonists, such as the compound of structural formula VIII disclosed in U.S. Pat. No. 6,017,926 (Jan. 25, 2000), which is useful to inhibit bone resorption and to treat osteoporosis.

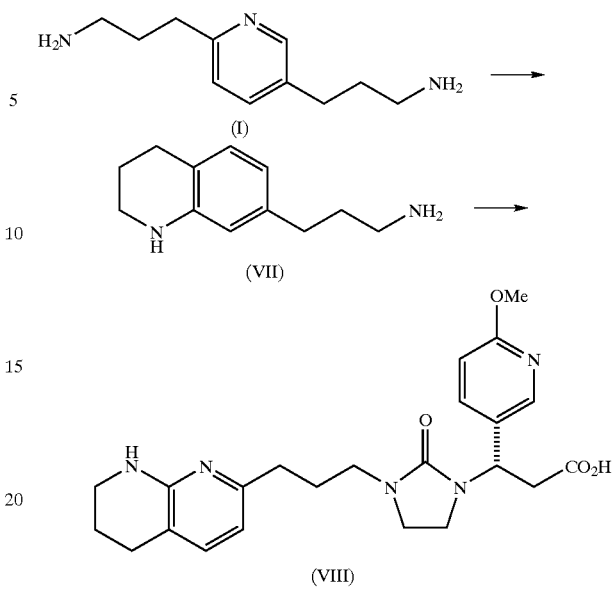

Representative experimental procedures utilizing the novel process of the present invention are detailed below. They are given for purposes of illustration only and are not intended to limit the process of the present invention to the specific conditions given for making the exemplified compounds.

By lower alkanol is meant a C$_{1-5}$ linear or branched-chain alkyl alcohol, such as methanol, ethanol, isopropanol, and 1-butanol. By halide is meant fluoride, chloride, bromide, and iodide. By halogen is meant fluorine, chlorine, bromide, and iodine. By acyl is meant C$_{1-4}$ alkanecarbonyl, arylcarbonyl wherein aryl is phenyl or naphthyl, and phenyl-C$_{1-3}$ alkanecarbonyl. By sulfonyl is meant C$_{1-4}$ alkanesulfonyl, wherein alkane is optionally substituted with one to three fluorine atoms; arylsulfonyl group, wherein aryl is phenyl or naphthyl; and phenyl-C1-3 alkanesulfonyl. By phosphoryl is meant di(C$_{1-4}$) alkanephosphoryl or diarylphosphoryl, wherein aryl is phenyl or naphthyl.

EXAMPLE 1

Step A:

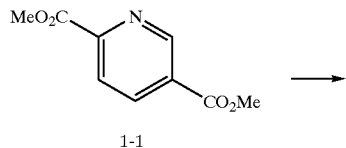

1-1

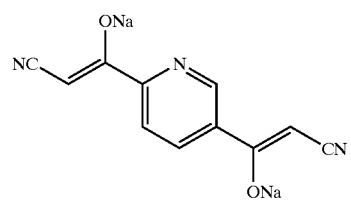

1-2

To a solution of dimethyl 2,5-pyridinedicarboxylate (1-1) (21.1 g) in acetonitrile (500 mL) at 60° C. was cautiously added sodium hydride (60% dispersion in mineral oil; 18.1 g). The reaction was allowed to cool and ethanol (30 mL) added. The product was isolated by filtration and washed with three portions of ethanol (50 mL). The solid was dried under a flow of nitrogen to afford 28.6 g of 1-2. $^1$H-NMR (400 MHz; DMSO-d$_6$): δ 8.61 (d, J=2.0 Hz, 1H), 7.84 (dd, J=8.0, 2.0 Hz, 1H), 7.66 (d, J=8.0 Hz, 1H), 4.57 (s, 1H), 3.99 (s, 1H).

Step B:

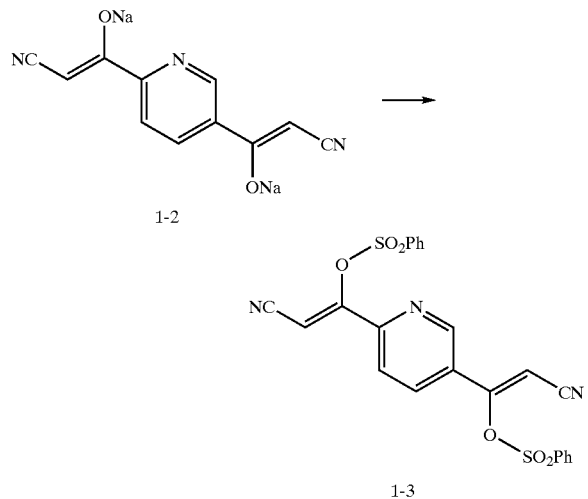

The bis sodium enolate from Step A (1-2)(28.4 g) was suspended in methanol (210 mL) with sodium carbonate (14 g) and cooled to 0° C. Benzenesulfonyl chloride (31 mL) was added and the reaction aged for 2 h. The slurry was filtered and washed with ice-old methanol (2×50 mL) to afford 61 g of 1-3. Two isomers, major listed: $^1$H-NMR (400 MHz; CDCl$_3$): δ 8.81 (d, J=2.4 Hz, 1H), 8.10 (dd, J=1.2, 8.4 Hz, 2H), 8.06 (dd, J=1.2, 8.4 Hz, 2H), 8.00 (dd, J=8.4, 2.4 Hz, 1H), 7.85 (d, J=8.4 Hz, 1H), 7.80 (m, 2H), 7.63 (m, 4H), 6.65 (s, 1H), 5.75 (s, 1H).

Step C:

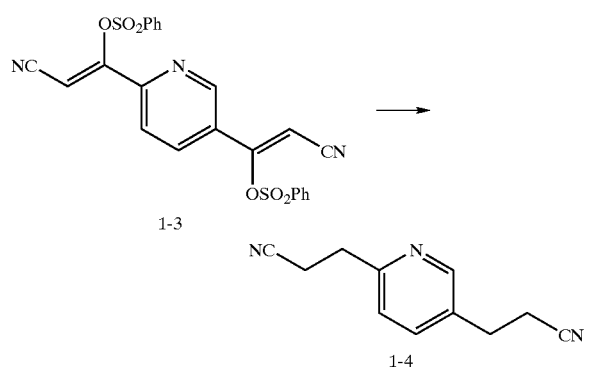

To a slurry of the bis-enol benzenesulfonate from Step B (1-3) in methanol (40 mL) was added with an additional 16 g of sodium carbonate, and the mixture was hydrogenated under 40 psi hydrogen at 20° C. in the presence of 10% Pd-C (1.0 g) for 32 h. The reaction mixture was filtered through a filter aid such as Celite® or solka floc® and concentrated under reduced pressure to afford 2,5-di(2-cyanoethyl) pyridine (1-4).
$^1$H-NMR (400 MHz; CDCl$_3$): δ 8.45 (d, J=2.0 Hz, 1H), 7.57 (dd, J=8.0, 2.0 Hz, 1H), 7.22 (d, J=8.0 Hz, 1H), 3.13 (t, J=7.2 Hz, 2H), 2.97 (t, J=7.2 Hz, 2H) J=7.2 Hz, 2H), 2.65 (t, J=7.2 Hz, 2H).

Step D:

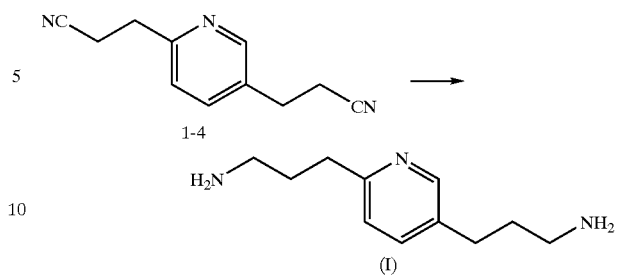

A solution of 2,5-di(2-cyanoethyl)pyridine from Step C (3.16 g) was dissolved in 7N ammonia in methanol solution (45 mL) and hydrogenated under 40 psi of hydrogen gas pressure at 50° C. in the presence of Raney nickel (1.6 g) for 20 h. The catalyst was filtered through solka floc® and washed with methanol. The filtrate and wash were combined and concentrated under reduced pressure to give 2,5-di(3-aminopropyl)pyridine (I)(2.95 g).
$^1$H-NMR (400 MHz; D$_2$O): δ 7.99 (d, J=2.0 Hz, 1H), 7.29 (dd, J=8.0, 2.0 Hz, 1H), 6.92 (d, J=8.0 Hs, 1H), 2.48 (t, J=7.7 Hz, 2H), 2.43-2.34 (m, 4H), 2.29 (t, J=7.7 Hz, 2H), 1.54 (pentet, J=7.7 Hz, 2H), and 1.42 (pentet, J=7.7 Hz, 2H).
$^{13}$C-NMR (101 MHz; D$_2$O): δ 158.7, 147.8, 137.6, 135.5, 123.0, 40.4, 40.2, 34.1, 33.5, 32.6, and 29.2.

What is claimed is:

1. A process for preparing the compound of structural formula I:

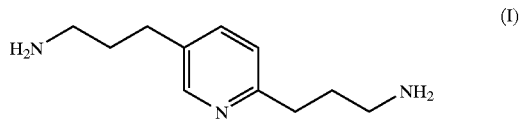

comprising (a) producing a compound of structural formula II:

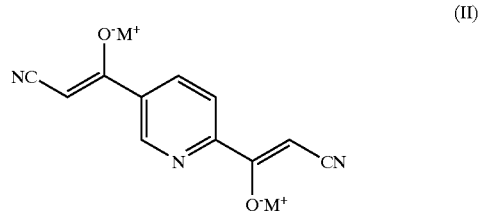

by treating a 2,5-pyridine dicarboxylate diester of structural formula III:

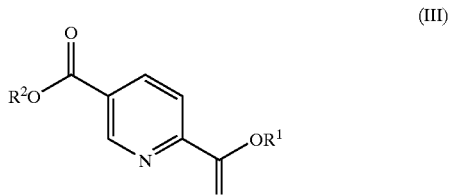

wherein R$^1$ and R$^2$ are each independently C$_{1-4}$ alkyl or phenyl-C$_{1-3}$ alkyl, with acetonitrile in a reaction solvent in the presence of a base; (b) producing a compound of structural formula IV:

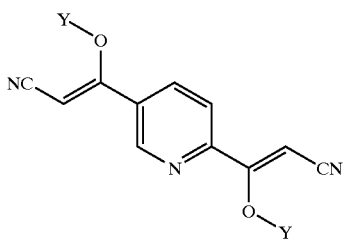

by reacting a compound of structural formula II:

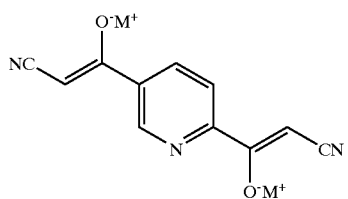

with an acylating, sulfonylating, or phosphorylating reagent;
(c) producing the compound of structural formula VI:

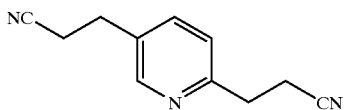

by hydrogenating a compound of structural formula IV:

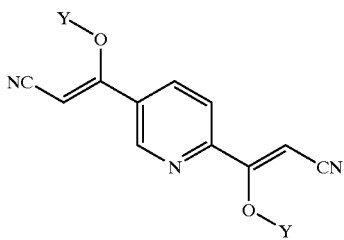

wherein Y is an acyl, sulfonyl, or phosphoryl group; and (d) hydrogenating the compound of structural formula VI:

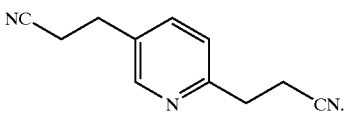

2. The process of claim 1 additionally comprising the step of producing a compound of structural formula II:

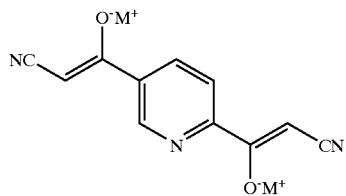

by treating a 2,5-pyridine dicarboxylate diester of structural formula III:

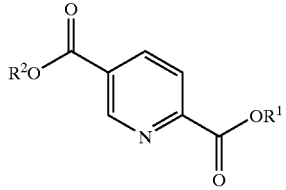

wherein $R^1$ and $R^2$ are each independently $C_{1-4}$ alkyl or phenyl-$C_{1-3}$ alkyl; with acetonitrile in a reaction solvent in the presence of a base.

3. The process of claim 2 wherein the base is selected from the group consisting of an alkali or alkaline earth metal hydride, an alkyl lithium, an alkali metal hexamethyldisilazide, and an alkali or alkaline earth metal alkoxide.

4. The process of claim 3 wherein the base is an alkali or alkaline earth metal hydride.

5. The process of claim 2 wherein the reaction solvent is selected from the group consisting of toluene, benzene, acetonitrile, dioxane, diethyl ether, tetrahydrofuran, and ethylene glycol dimethyl ether.

6. The process of claim 5 wherein the reaction solvent is acetonitrile or ethylene glycol dimethyl ether.

7. The process of claim 1 wherein the sulfonylating reagent is benzenesulfonyl chloride or benzenesulfonic anhydride optionally substituted with one or two groups independently selected from halogen, nitro, cyano, methyl and methoxy.

8. The process of claim 1 wherein the reaction is carried out in the presence of a buffer.

9. The process of claim 1 wherein in (d), the hydrogenation is carried out in the presence of a Raney nickel catalyst and ammonia.

10. The process of claim 1 wherein in (c), the hydrogenation is carried in the presence of a palladium catalyst and base.

11. A compound of the structural formula:

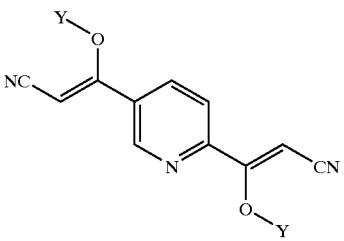

wherein Y is $C_{1-4}$ alkanoyl, benzoyl, naphthoyl, phenyl-$C_{1-3}$ alkanoyl, $C_{1-4}$ alkanesulfonyl optionally substituted with one to three fluorines, benzenesulfonyl, di-($C_{1-4}$ alkyl)

phosphoryl, and diphenylphosphoryl, wherein the benzene, benzoyl, naphthoyl, and phenyl groups are unsubstituted or substituted with one or two substituents independently selected from halogen, nitro, cyano, methyl, and methoxy.

12. The compound of claim 11 wherein Y is benzenesulfonyl optionally substituted with one or two substituents independently selected from halogen, nitro, cyano, methyl, and methoxy.

13. A compound of structural formula VI:

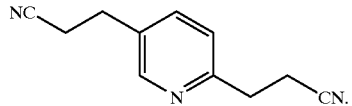

(VI)

* * * * *